(12) United States Patent
Echner

(10) Patent No.: US 7,783,007 B2
(45) Date of Patent: Aug. 24, 2010

(54) IRRADIATION DEVICE AND COLLIMATOR

(75) Inventor: Gernot Echner, Wiesenbach (DE)

(73) Assignee: Deutsches Krebsforschungszentrum Stiftung des öeffentlichen Rechts, Heidelberg (DE)

(*) Notice: Subject to any disclaimer, the term of this patent is extended or adjusted under 35 U.S.C. 154(b) by 616 days.

(21) Appl. No.: 11/795,509

(22) PCT Filed: Jul. 27, 2006

(86) PCT No.: PCT/EP2006/007471

§ 371 (c)(1),
(2), (4) Date: Jul. 18, 2007

(87) PCT Pub. No.: WO2008/011900

PCT Pub. Date: Jan. 31, 2008

(65) Prior Publication Data

US 2010/0054408 A1 Mar. 4, 2010

(51) Int. Cl.
*A61N 5/10* (2006.01)
*G21K 1/04* (2006.01)
(52) U.S. Cl. ............................. 378/65; 378/150
(58) Field of Classification Search ............. 378/62, 378/64, 65, 147–159
See application file for complete search history.

(56) References Cited

U.S. PATENT DOCUMENTS

| | | | |
|---|---|---|---|
| 2,675,486 A | | 4/1954 | Green et al. |
| 2,959,680 A | * | 11/1960 | Green ........................ 378/152 |
| 3,973,127 A | * | 8/1976 | Matsuda et al. ............... 378/24 |
| 5,204,892 A | * | 4/1993 | Warden ...................... 378/152 |
| 6,730,924 B1 | | 5/2004 | Pastyr |
| 7,132,674 B2 | | 11/2006 | Pastyr |
| 2006/0067481 A1 | * | 3/2006 | Morton ........................ 378/151 |
| 2009/0074148 A1 | * | 3/2009 | Echner ........................ 378/152 |

FOREIGN PATENT DOCUMENTS

DE 1 037 035 8/1958

(Continued)

*Primary Examiner*—Irakli Kiknadze
(74) *Attorney, Agent, or Firm*—Paul Vincent

(57) ABSTRACT

An irradiation device for radiation treatment and a collimator (1) are used to define a beam of high-energy rays (2) with beam limitation by means of an iris diaphragm (5) having adjusting elements (7), and a mechanism that is used to direct the beams (2') limited by the collimator (1) to the object to be treated (4) from all sides, wherein the parameters for direction, surface area, intensity and time of irradiation can be specified with the help of a control mechanism. An exact three-dimensional irradiation profile is produced, while keeping the costs and efforts regarding mechanical engineering, computation and irradiation time low. This is achieved by using at least one further iris diaphragm (6) located in coaxial alignment in the optical path, whereby the leaves (9, 9', 9'', 9''', 9'''', 9''''') of the iris diaphragms (5, 6) are arranged in a staggered manner and in a rotational sense around their axis (11), so that the beam limited by the collimator (1) has the cross-section of a polygon (12), the number of corners of which complies with the number of the leaves of all iris diaphragms (5, 6), so that the leaves (9, 9', 9'', 9''', 9'''', 9''''') allow for linear adjustment movements (13), the control mechanism being suitable to enable the irradiation of an irregular space through the overlaying and adjoining of many irradiated spaces (28).

29 Claims, 7 Drawing Sheets

FOREIGN PATENT DOCUMENTS

| | | |
|---|---|---|
| DE | 1 564 765 | 1/1970 |
| DE | 15 89 432 | 7/1970 |
| DE | 2 053 089 | 5/1972 |
| DE | 199 22 656 | 12/2000 |
| EP | 0 382 560 | 8/1990 |
| FR | 2 088 185 | 1/1972 |
| FR | 2 088 186 | 1/1972 |
| FR | 2 524 690 | 10/1983 |
| JP | 60 185 567 | 9/1985 |
| JP | 04 208 140 | 7/1992 |
| JP | 07 047 142 | 2/1995 |

\* cited by examiner

IRRADIATION DEVICE AND COLLIMATOR

This application is the national stage of PCT/EP2006/007471 filed on Jul. 27, 2006.

BACKGROUND OF THE INVENTION

The invention relates to an irradiation device with a collimator used to define a beam of high-energy rays proceeding from an essentially punctiform radiation source and directed to an object to be treated, and which serves for radiation treatment, in particular the stereotactic conformation radiotherapy of tumors, whereby the collimator is realized by means of iris diaphragms with adjusting elements so as to provide for variable apertures for beam collimation, and a mechanism that shall be used to direct the beams limited by the collimator to the object to be treated from all sides, and whereby the parameters for direction, surface area, intensity and time of irradiation can be controlled in such a manner that a three-dimensional dosing profile for radiation application can be achieved.

Furthermore, the invention relates to a collimator used to define a beam of high-energy rays proceeding from an essentially punctiform radiation source and directed to an object to be treated, and which serves for radiation treatment, in particular the stereotactic conformation radiotherapy of tumors, whereby the collimator is realized by means of iris diaphragms with adjusting elements so as to provide for variable apertures for beam collimation.

Irradiation devices with collimators for the restriction of a beam of high-energy rays are used, above all, in the therapy of tumors. Collimators are also used in imaging systems, such as X-ray devices. In this context, collimators are used to restrict the beam so as to provide best possible protection of healthy tissue in the vicinity of the area to be diagnosed or treated and to avoid damage to this tissue or to reduce the damage to a minimum.

Application must be differentiated into diagnostic and therapeutic radiation. The energy of the former must be low enough to prevent damaging of the tissue, if possible. These rays are only used for the purpose of image generation, for example, in the course of irradiation treatment preparation, so that the doctor can visualize the position of a tumor, as well as the surrounding and possibly critical tissue, such as nerves. Since the surrounding tissue must be visible, some areas outside the tumor or other sections to be diagnosed must also be exposed to radiation. Since in most cases the tumors or other areas to be diagnosed are round in shape, the imaging field should be circular as well and, of course, it should not exceed the area of interest to the doctor, as X-rays are also harmful to the tissue. Therapeutic radiation, however, must have an energy level that allows the destruction of diseased tissue, such as tumors. Consequently, this radiation would also destroy the surrounding tissue. For this reason, the shielding should be suitable to limit the beam to exactly the shape of the affected tissue.

When applying high-energy therapeutic rays—which is the intended purpose of the invention-specific irradiation device and collimator—major importance is attached to the protection of the surrounding tissue, since the patient's quality of life after treatment often depends on this aspect. Side effects of irradiation through the impairment of healthy tissue cannot be absolutely excluded, however, they should be reduced to a technically feasible minimum. Since this is of essential significance and, in contrast to irradiation with X-rays, has very serious consequences even in the case of short-time exposure, the development of irradiation devices offering an increased accuracy in radiation application has been pursued by experts for many decades, so as to reduce the negative side effects of radiotherapy as far as possible.

Originally, the irradiation devices and imaging devices were equipped with collimators that could restrict the irradiation field in size but not in shape. As regards image-generating X-rays this does not imply any major consequences for the patient, since X-rays are harmful only after long exposure, which is not required for imaging, or if the patient is exposed to X-rays very frequently within a short period of time. Only high-energy therapeutic radiation—as required, for example, for the destruction of tumor tissue—will cause damage to healthy tissue in the over-range irradiation area, i.e. outside the tumor tissue to be irradiated, since radiation must be applied at a certain intensity and over a certain period of time required to destroy the tumor issue.

These over-range irradiation areas were caused by missing or insufficient imaging of the contour of the tumor tissue by the collimators and resulted from the occurrence of penumbrae at the borders of the area to be irradiated, since the shielding material was not in parallel alignment with the rays so that it could not provide full shielding, in particular when large areas were to be irradiated. With high-energy therapeutic beams, these penumbrae affected much larger areas, since the required thickness of the shielding is a multiple of that required for X-rays with a comparatively low radiation level. Furthermore, many irradiation devices showed leakage radiation emitting through the gap between adjacent shielding plates.

One example of a collimator restricting the beam only in size is an older model according to U.S. Pat. No. 2,675,486. This publication refers to a collimator for high-energy beams and equipped with four beam collimating blocks which can be displaced in one plane with the help of adjoining side faces, so that a square beam collimation in different sizes can be achieved. As tumors, however, are normally not square-shaped but have mostly a round shape, the over-range irradiation area at the corners was quite large. Moreover, large irradiation fields involved large penumbrae, since the block collimators were no longer in parallel alignment with the diverging optical path.

For this reason, experts made an effort to defuse these problems.

Based on a collimator of the type described above, the publication DE 20 53 089 A1 suggests, for the field of X-ray imaging, use of a shielding structure in the form of adjacent triangles, and to use this iris-type collimator design to achieve an approximately circular irradiation field—which comes closer to the shape of the area to be actually irradiated—so that the excess irradiation of approx. thirty percent caused by the corners of the previously square-shaped beam collimation can be avoided. The remaining excessive irradiation area and the formation of penumbrae is not a serious problem, since radiation refers to X-rays for imaging purposes, but not to therapeutic irradiation with beams of much higher energy. As the diaphragm leaves used for X-raying are considerably thinner than those for therapeutic radiation, it is sufficient to provide the proposed iris-type collimator with diaphragm leaves located near the focus which only roughly collimate the beam emitted from the radiation source by preventing afocal rays in the plane of the anode disk of the X-ray source, so as to avoid the emission of radiation from the device to the surrounding environment. By its collimation to a round irradiation field, the beam is sufficiently restricted, since the radiation for imaging purposes should not at all be limited as exactly as a therapeutic beam. After all, the neighboring tissue shall also be displayed so that the doctor can assess the position of the tumor in relation to the surrounding tissue.

For the use of ionizing, i.e. high-energy beams suitable for tumor treatment in this context, publication DE 15 89 432 A1 suggests the use of a collimator with adjacent wedge-shaped radiation shielding units that can be shifted in one plane so as to enable the formation of hexagonal, octagonal or rectangular openings, i.e. a polygon according to the number of diaphragm leaves. However, this type of collimator represents the shape of a tumor quite insufficiently and it does not offer a solution for the formation of penumbrae caused by the front edges of the diaphragm leaves which are not aligned in the direction of the optical path. The prevention of leakage radiation is also insufficient. Although the areas where the diaphragm leaves meet are provided with inset tongues, these tongues are too thin for an effective shielding of radiation emitting through the gap between adjacent leaves. If large irradiation fields are to be treated where the optical path is quite sloping in relation to the borders of the shielding material, the penumbra region will be quite large.

DE 10 37 035 B also refers to a collimator of the type stated in the first-mentioned publication and suggests, for high-energy therapeutic beams, to divide the four beam collimating blocks into two parts along an oblique line, whereby the line shall extend to that point where the inner and end surface (i.e. the surface adjacent to the next block) meet. This will divide each block into a primary and a secondary part which can be shifted towards each other. This allows the formation of different contours and reduces the amount of exceeding radiation compared to square-type radiation collimation. This type of reconstruction of the tumor shape or any other area to be irradiated is certainly quite inadequate and the penumbra problem also remains unsolved. It is soley the problem of leakage radiation that is prevented by the mutual dovetail-type guides in the bordering areas of the diaphragm leaves.

One solution for the penumbra problem is, after all, stated in DE 15 64 765 A1. This publication also sets out from a collimator of the same type as described in the first-mentioned publication with four adjacent radiation restricting blocks which each can be moved in one plane. This system is aimed at achieving a clearly outlined field, i.e. an area without penumbrae. For this purpose it is suggested to design the blocks with swiveleable bearings and a mechanism that ensures that the guiding ends that form the border for radiation will be oriented towards the radiation source in each setting. In this way, the radiation will be fully shielded by the material of the blocks. However, this collimator only allows formation of square-shaped irradiation fields, so that large exceeding radiation areas at the edges had to be accepted.

Both the problem of leakage radiation and the penumbra problem are dealt with in FR 2 524 690 A. For the prevention of penumbrae, this publication suggests the use of adjacent plates each of which can be moved in one plane and simultaneously be turned, whereby the different plates are arranged in several planes, so that a graded beam collimation aperture in the shape of a frustum of a pyramid can be achieved. With this structure, the formation of penumbrae can be avoided to a large extent. Leakage radiation is prevented, because the contact points of adjacent plates no longer align, since the individual apertures are in different planes. In closed condition, however, they will still be aligned, so that the radiation source must be switched off or shielded in this state. One disadvantage of this collimator is the intricate mechanical design required for the correct shifting and simultaneous turning of the plates in all planes so as to achieve a beam collimation aperture in the form of the frustum of a pyramid. One further disadvantage of this solution is that the collimation field for irradiation can only be formed on the basis of polygons—depending on the number of plates—but the real tumor contour cannot be accurately defined. Because of the intricate mechanism, a quadrangular beam collimation will be favored. This shape, however, deviates considerably from the real contour of the tumor.

To improve the imaging of the tumor shapes and, in particular, to reduce exceeding irradiation to a minimum when using shielding material of the relevant thickness, one proceeded to the use of exchangeable fixed collimators. With this technique, the tumor shape was captured from different three-dimensional directions, but it required the production of several fixed collimators for each irradiation treatment which could then be used for irradiation from different directions. This included the advantage of accurate contouring and the possibility of adjusting collimation exactly to the optical path so that no penumbra occurs. The disadvantages included the complicated procedure with the continuous exchange of collimators, a prolonged use of expensive devices, as well as the costs for the production of a large number of collimators for each irradiation process; these collimators could not be used any further, since they were designed for one specific patient and could be used only within a very limited time frame even for this patient; the latter resulting from the continuous change of a patient's tumor by growth, regression or deformation.

In order to minimize these costs and efforts, multileaf collimators with a large number of tiny, closely adjacent leaves were created which were suitable to image the tumor by adjusting the leaves accordingly. At first sight, these multileaf collimators had the advantage of a quick setting for any type of shape, however, the mechanical design with the adjusting elements for each leaf was a considerable disadvantage, as well as the more or less large penumbra which occurred at each border of the irradiation field caused by a leaf, depending on its distance from the axis of the optical path.

EP 1 153 397 B1 suggested to prevent the occurrence of penumbrae by providing the leaves with adjustable front edges, whereby a specific mechanism ensures their parallel alignment with the optical path. This, however, requires an even more complicated mechanical structure of the multileaf collimator.

In order to avoid these intricate mechanisms and to increase the flexibility in the shaping of the surface to be irradiated, the publication DE 199 22 656 A1 suggested a scanning system with a collimator aperture which is small enough to irradiate the areas of the object to be irradiated with sufficient precision (FIG. 3). Although the collimator opening of the above proposal is small enough and prevents the formation of penumbrae, it requires extensive time for the scanning process—with a large diaphragm aperture the scanning process can be completed earlier, but the required accuracy cannot be achieved. The use of multiple-hole plates to generate a beam of several scanning rays (FIGS. 5 and 5a) did not lead to satisfactory time reduction. The multiple-hole plate was not flexible with regard to the surface to be irradiated and for an exact irradiation of the marginal areas even smaller apertures had to be used, i.e. the plates had to be exchanged.

In order to increase the scanning speed without reducing the high level of accuracy, the publication DE 101 57 523 C1 suggested the use of a collimator with several collimator apertures of different size which can be brought into the optical path as desired. This was preferably effected with the help of a revolving turret-type mechanism that turned a round plate with different apertures. The high-energy rays as applied in radiotherapy today require a shielding material of 6 to 10 cm in thickness. This leads either to a collimator of considerable weight or the number of aperture sizes must be limited, for example, to three openings. But even with these restrictions, the unused apertures must be covered so as to avoid deficiencies in the shielding of areas through insufficient material thickness. Apart from the plate with the apertures, this system requires an additional shielding plate, also of several centimeters in thickness. For this reason the collimator will be relatively heavy, thus increasing the requirements on guides and drives accordingly. The above stated reasons involve a further disadvantage of this collimator, since only a few defined collimator apertures are available so that the variability of beam collimation is quite limited. In particular, the reduced number of openings makes it impossible to use large apertures of different diameters which could be used to treat one larger surface of the area to be irradiated first and then to irradiate the marginal areas with graded, smaller beams. Since the exposure time for radiation application is several seconds for each point on a surface, the scanning of a surface with fixed beam parameters requires more time than with optimal adjustable values. This applies, in particular, if the beams are narrower than would be possible with regard to the irradiation surface. This leads to an extension of the total treatment period. This is not only inconvenient for the patient who must be immobilized, but it also reduces the number of treatments possible with one device—an aspect of great economic significance in view of the high purchasing and operating costs of these devices. Apart from this, the application accuracy in marginal areas is limited, which is critical if areas with nerves are in the vicinity.

Eventually, EP 0 382 560 A1 suggested an irradiation device of the same type as described at the beginning of this document. This publication refers mainly to a combination of imaging and irradiation treatment. Among other things, it proposes the use of a collimator with an iris diaphragm which offers quite a variable configuration of the aperture. The iris diaphragm, however, produces a polygonal cross-section for the beam. An application from different directions will transform this polygonal cross-section, for example, into a hexagonal shape so that the three-dimensional orientation will continuously change and would have to be included in the calculation of the application with regard to spatial angle, aperture size and irradiation period. This would cause a considerably increased complexity with regard to the calculation of the great number of individual irradiations to be applied—which often sum up to more than one hundred for one single irradiation session—and when considering the above-stated parameters aimed at achieving a specific three-dimensional irradiation profile. But even if the different orientations of the polygonal beam shape were accepted without eliminating them, this would lead to errors in the irradiation profile applied. These errors would increase with the deviation of the polygonal shape from a circular form. Of course, an iris diaphragm could be equipped with more leaves, so that the polygon could be included in calculation as a circle without causing major inaccuracies; this would considerably simplify the calculation process so that the computer capacity and/or computing time could remain within acceptable limits. As a consequence, however, integration in one diaphragm would require enormous mechanical efforts which, from a certain number of diaphragm leaves including drive and guide mechanisms for each leaf, would soon reach the limit of spatial accommodation.

In addition, the solution suggested in EP 0 382 560 A1 shows some further problems:

In order to shield high-energy therapy radiation with a energies in a megavolt range as used today, the shielding material, most often made of tungsten, must have a thickness of between 6 and 10 cm. Since as many leaves as possible shall be used, the thickness of these leaves does not allow to put them in multiple layers one on top of the other. It is therefore necessary to provide them with adjacent side faces as proposed in many of the above-stated publications. Even if these side faces are intricately worked, a small gap will remain and cause an emitting of leakage radiation. This could be prevented by tongues covering the gap as proposed in DE 20 53 089 A, but in view of the great number of required leaves this would increase complexity and require further installation space, since the tongues must be adequately thick so as to ensure adequate shielding properties.

The big advantage in using this type of iris diaphragm, i.e. the formation of beams with different cross-sectional areas—thus offering a significant reduction in the total irradiation time—is at the same time its disadvantage: depending on the aperture size, the beam collimating areas of the iris diaphragm are simultaneously the sliding surfaces between the individual leaves. This means that they must be mainly in perpendicular alignment to the optical path with only minor deviations. When using shields with a leaf thickness of between 6 and 10 cm, a wide-open iris diaphragm has the effect that the rays in the outer beam region will considerably diverge and can be shielded only to some extent, since they are partly outside the material. The rays passing completely through the aperture will be surrounded by a sort of halo, i.e. the penumbra stated further above, that reaches up to the fully shielded area. With an irradiation device of the type described at the beginning of this document, a larger degree of associated irradiation of the surrounding tissue must be accepted—which is, of course, intolerable from a medical point of view—or the marginal areas must be scanned with a very thin beam with only little penumbra formation and which must be graded in such a way that the penumbrae applied by the large beam can be eliminated again as exactly as possible. However, this procedure would multiply the time required for processing and computation.

Apart from the use of an X-ray scanner for image generation, the most significant disadvantage of the irradiation device according to EP 0 382 560 A1 is, however, that it mentions a type of "scanning movement" by the therapy beam which is put into more concrete terms only insofar that an attempt is made to use the iris diaphragm to gain an approximate image of the object's shape by the form of the beam cross-section from each spatial angle. This implies only an overlay of the individual applications from different spatial angles but not a combination of individual applications as performed with the scanning procedure described in DE 199 22 656 A1 and DE 101 57 523 C1. Although this enables the formation of a round irradiation area, as well as the formation of irradiation regions with an elliptical cross-section (as shown in FIG. 4 of the above-mentioned publication), irregular regions, which the object to be treated usually are, cannot be achieved by a combination of individual applications in this manner.

Hence, one basic objective of the invention is to further develop an irradiation device and a collimator of the type described above, so as to generate a three-dimensional irradiation profile that can be applied with greatest possible accuracy and with maximum protection of the surrounding tissue while the mechanical efforts and the time required for computing and irradiation are kept to a minimum.

SUMMARY OF THE INVENTION

According to the invention, this task is solved by at least one further iris diaphragm located in coaxial alignment in the optical path, whereby the leaves of the iris diaphragms are arranged in a staggered manner and in a rotational sense around the axis, so that the beam limited by the collimator represents the cross-section of a polygon the number of corners of which complies with the number of the leaves of all iris diaphragms, so that the leaves have adjacent side faces enclosing the same angles, whereby the adjustment movements of the diaphragm leaves are linearly perpendicular to the angle bisector of the side faces engaged in the adjacent diaphragm leaves, the control mechanism being suitable to enable irradiation of an irregular space by many overlaying and adjoining irradiated spaces.

According to the invention, this task is solved by at least one further iris diaphragm being located in coaxial alignment in the optical path, whereby the leaves of the iris diaphragms are arranged in a staggered manner and in a rotational sense around the axis, so that the collimated beam represents a polygonial cross-section the number of corners of which complies with the number of the leaves of all iris diaphragms, so that the leaves have adjacent sides enclosing the same angles, whereby the adjustment movements of the diaphragm leaves are linearly perpendicular to the angle bisector of the side areas engaged in the adjacent diaphragm leaves.

With regard to the further elaborations on the collimator, please refer to the description of the irradiation device as far as it refers to the collimator.

The invention is based on an irradiation device for radiation applications from different directions in order to irradiate the tissue to be with considerably more intensity than the surrounding tissue. This is to protect the healthy tissue and to destroy the diseased tissue. Furthermore, the invention refers to an irradiation device with a corresponding collimator, whereby the collimator does not represent the shape of the object to be treated, but uses a sort of three-dimensional scanning process which, however, uses beams of different sizes in order to reduce the irradiation time. This method allows to irradiate larger areas of the object to be treated with larger beams, followed by irradiation with increasingly smaller beams so as to achieve an exact tracing of the object to be treated. The beams may be applied in fixed position from different directions for a predefined period of time, or the irradiation area may be moved over the object to be treated. This not only leads to an overlay of many irradiated three-dimensional areas, but these areas are also joined or joined with partial overlays, whereby a dosing profile can be achieved that complies with the intensity required for treatment within an irregular space. This enables generation of a spatial irradiation profile, whereby—as far as necessary under medical aspects—different intensity profiles can be applied. Critical areas in the vicinity, such as nerves, can be completely avoided.

One important element of the invention with regard to both the irradiation device and the collimator is the minimum of two coaxial iris diaphragms located in the optical path for the purpose of an adjustable beam limitation. This element requires some further elaboration, so as to solve the technical problems of the previous state-of-the art system described at the beginning:

First of all it is, of course, necessary that the diaphragm leaf sides have adjacent side faces enclosing the same angle. This is a precondition to construct iris diaphragms of the required shielding capacity. Usually, the shielding material for these rays, e.g. made of tungsten, has a thickness of 6-10 cm. So, even if this material were distributed over several iris diaphragms, the leaves would still be too big for an overlapping arrangement of one on top of the other.

Especially when a great number of individual irradiations from different directions shall be applied, but also when beams shall be moved slowly over the object to be treated, this application of a predefined spatial irradiation profile requires inacceptably high computational time, even if the beams are polygons with relatively few corners, as for example a hexagonal shape, and if this polygon and its continuously changing alignment would have to be included in this calculation process. For this reason, one essential characteristic of the invention is that the leaves of the iris diaphragms are displaced in an opposite arrangement in rotational direction, so that the collimated beam represents a polygonal cross-section, whereby the number of corners of the polygon corresponds to the number of the diaphragm leaves of all collimators. In doing so, the rays can be restricted by polygons which come close to a circular form so that they can be included in the calculation as a circle without causing intolerable deviations from the predefined irradiation profile and could be accepted from the medical point of view. The use of two iris diaphragms allows to generate a polygon with twice the number of corners as is possible with each single iris diaphragm alone; if more iris diaphragms are used, the number will increase accordingly. This enables the generation of a polygonal shape with a great number of corners without requiring iris diaphragms with too many leaves which would be difficult to be accommodated within the mechanical structure, in particular the required drives and guides. Furthermore, the production of a larger number of simply constructed iris diaphragms is more cost-effective than a small number of iris diaphragms of a considerably more complicated design. One preferred design version would be the arrangement of two six-leaf iris diaphragms which allow for a twelve-cornered beam collimation and which would usually meet the specified purpose. Of course, an 18-cornered beam collimation could also be achieved with the help of three iris diaphragms of this type or even higher corner numbers would be possible, if continued in this manner.

Concomitantly, this arrangement solves the problem of leakage radiation: The use of iris diaphragms of the type mentioned above—as already described in the introduction—bears the problem of more or less large gaps at the borders between the diaphragm leaves, since an absolute matching of the surfaces cannot be realized in practice. Usually, the actual limit of absolute surface matching is below what would be technically feasible, since a cold-welding process is not possible. Apart from this, the manufacturing costs must also be kept within affordable limits. Since the leaves of the iris diaphragms are staggered in the direction of rotation, all leakage rays will be shielded by one or more further iris diaphragms. Since the leakage radiation emitting through the small gaps is quite low, only half of the material thickness will be required for shielding. When three iris diaphragms are used, even two thirds of the total shield thickness would be obtained.

The beams from the radiation source shall, however, not only be directed to the treated object from all sides, as with collimators imaging the shape of the tumor more or less exactly as, for example, described in EP 0 382 560 A1, but a three-dimensional irradiation profile shall be generated, whereby many irradiation areas of different sizes must be joined in an overlaying, adjacent and often in a partly overlapping manner. This requires a system equipped with a collimator consisting of several iris diaphragms that is capable of orientating the radiation source to various positions within a three-dimensional area for a short time, whereby the spatial arrangement, as well as the alignment in a specific spatial angle must be included. This may be effected either in steps or in a continuous process. Such an irradiation head consisting of the radiation source, shielding and in particular the collimator must be kept as small as possible in weight and size. In consideration of technical and economic aspects, this means that a complicated adjustment mechanism of the diaphragm leaves by combined turning and shifting movements as suggested in FR 2 524 690 A is not a reasonable solution.

For this reason, the invention proposes that the diaphragm leaves have adjacent sides enclosing the same angles, whereby the adjusting movements of the leaves are performed only linearly perpendicular to the angle bisector of the side faces of the adjacent diaphragm leaves. This has the advantage of simple actuation of each diaphragm leaf along a straight guiding line, whereby all leaves of an iris diaphragm move synchronously. The leaves of the further iris diaphragm (s) are adjusted simultaneously. This helps to realize uncomplicated drive and adjusting elements and the guides can be implemented in a simple linear design. In particular the drive, guide and adjusting elements can be accommodated in one irradiation head while this irradiation head remains small and light enough to bring it easily into different positions and alignments in a three-dimensional area, which is an essential requirement for a system according to this invention.

In this manner, the above-stated task can be solved with an irradiation device of reasonable construction size and weight, whereby these factors also effect the size of the drive, the required drive energy and the speed of control. Apart from the reduced engineering efforts and the computer hardware and software requirements, this method also provides savings in weight and energy. In particular the adjusting and computation times that are not used for irradiation application can be minimized, so that the overall period required for treatment will be reduced. The invention combines these advantages with a maximum protection of the healthy tissue during radiation application, so that the risks for the patient can be further minimized.

The distribution of the required thickness of the shielding material over several iris diaphragms also supports a reduced construction height of the individual diaphragm leaves and, in doing so, offers better linear guidance of the leaves, improved contiguousness of adjacent leaf sides and, in particular, a reduced risk of unparalleled joining of tilted leaves.

The above-stated coaxial arrangement of the iris diaphragms also helps reduce the occurrence of penumbra in a most simple manner by designing the adjusting elements of the iris diaphragms in such a way that beam collimation by the relevant apertures corresponds to the divergence of the beams within the total adjusting range. In this way the shielding will be graded in relation to the divergence of the rays. With regard to the leaves of the iris diaphragms forming the collimator, the adjustment distance of the leaves of an iris diaphragm located closer to the radiation source is shorter than that of leaves of one or more iris diaphragms located at a greater distance. However, this measure will be required only, if the apertures are sufficiently large that a significant beam divergence is given. When very small apertures are used, the divergence of the beams and possible penumbrae are negligible. Consequently, these apertures are suitable for most critical limit ranges, e.g. in the vicinity of nerves, so as to ensure exact restriction of the area to be irradiated after previous treatment of the larger areas with broader beams.

The design of the collimator should preferably include that the identical number of leaves of at least two iris diaphragms allows an angle displacement of the iris diaphragms in the same rotational sense around their axis, as well as the formation of the cross-section of an equilateral polygon through the design of the adjusting elements, as this comes closest to a circular shape. Since the adjustment distances of the leaves of the relevant iris diaphragms, as well as the adjusting distances of all individual iris diaphragms are matched accordingly with the beam divergence over the whole setting range, the beams will form this equilateral polygon independently of its size.

The control unit should preferably be designed in such a way that different aperture sizes, different positions of the radiation source and the collimator in a three-dimensional area and the alignment in certain spatial angles are suitable to combine single applications that capture a great number of only limited partial spaces of the object to be treated, so that an irregular spatial shape can be reproduced by a mainly circular beam cross-section, so as to enable irradiation of this area within relatively accurate borders and with a significantly higher intensity than applied to the surrounding tissue. This is effected with a sort of spatial scanning process, whereby the shape of the partial spaces treated usually differs greatly from the shape of the overall object to be treated, whereby, compared to the common scanning of surfaces which is mostly performed linewise over the surface with a beam of constant size, the scanning process here is performed in relation to a specific space and with beam cross-sections of different sizes. Furthermore, scanning is not performed linewise but through the interlacing of many beams of different sizes according to a previously calculated scheme. This interlacing refers to both adjacent and overlaying positions including partially juxtaposed or overlapping space segments of the single applications. Due to the different space sizes of the single applications it is possible to accelerate the irradiation of larger areas and to treat the remaining areas with increasing precision until all of the almost always irregular spatial shape of the object to be treated has been irradiated at the specified intensity. This method also allows to generate irregularly shaped irradiation spaces of different intensity levels.

This radiation application is preferably practiced by using single applications over a certain period with unchanged parameters. This bears the advantage that the application process is not disturbed by mechanical adjustment operations so that the required tolerances can be observed more easily.

The realization of application can be imagined in such a way that each single application captures a cylindrical area that extends through the whole human body. These cylindrical areas differ in size and come from all possible directions and intersect within the area of the object to be treated, so that this area will be exposed to radiation dose which is a multiple of that applied to the surrounding tissue. This corresponds to the image of filling a room with numerous cylinders of different size which are not only aligned differently within the space but occupy the space multiplicatively. Especially this combination of juxtaposed and overlaying positions and the combination of both in the area of the object to be treated produces the required increase in the irradiation intensity, whereby the surrounding tissue remains as unaffected as possible or will at least be able to regenerate, whereas the tissue to be treated, e.g. the tumor, will die off. Accordingly, it is also possible to avoid critical areas, such as nerves, at the margins of the object to be treated so that, if possible, no direct radiation will impinge on these regions.

One particularly useful aspect of the invention refers to the design of the iris diaphragms. In this context best contiguousness of the diaphragm leaves is achieved through the application of force that presses the side faces of the leaves together. This can be achieved, for example, if the diaphragm leaves consist of a shielding element made of shielding material and a bearing element, whereby the bearing element is provided with a guide element of a linear guiding mechanism for the adjustment movement, and the shielding element on the bearing element is supported with springs, so that it will be pressed evenly towards the direction of the adjacent diaphragm leaves. This structure has a great number of advantages: exact surface contact is ensured as the side faces always border each other evenly so that a possible gap can be caused only by an uneven or rough surface condition. Proper surface contact is guaranteed even in case of certain dimensional variations, so that no special requirements on production accuracy must be demanded which would lead to far higher prices. This makes the irradiation device considerably less expensive. Furthermore, jamming of the diaphragms and/or the adjusting mechanism can be excluded as far as possible, even if it comes to a certain deviation in tolerance. Also, it is improbable that this jamming will occur at a later point, for example as a result of wear, dirt, minor damage or thermal expansion. This not only reduces the costs of production, but also offers considerable improvement in the functional safety of the device.

The irradiation head that consists of the radiation source and the collimator, may be positioned on a gantry that enables irradiation of the object to be treated from different directions. Preferably, however, the irradiation head including the radiation source and the collimator, is mounted to a robot arm designed to maneuver the irradiation head into any position and angular alignment within a three-dimensional area. Compared to the previous arrangement of the irradiation heads on a gantry, the use of a robot arm offers the advantage of a considerably greater multitude of spatial positioning and alignment. Being mounted on a gantry, the irradiation head circulates around a center where the object to be treated is positioned. Further variations are possible only if the position of the patient is slightly changed, so that the focus can be brought to different positions on the object to be treated. In contrast, a robot arm does not need to be focused to a center, as it can be directed to any coordinates and spatial alignment or to any desired combination thereof, whereby the only restriction is the specific construction of the robot arm, which is, however, much less a limitation in positioning than that imposed by a gantry. Consequently, the robot arm offers a considerably higher degree of freedom in adjustment, so that optimum use can be made of the multiplex adjoining, overlaying and interlacing of partial spaces of different size as required by the single applications, and critical areas, such as nerves, can be better avoided.

To enable very quick and precise scanning of the beam position, the collimator may be installed on a track with a spherical surface, so that it can be shifted in all directions for pivoting motions within a limited spatial angle range, whereby the axis must always be oriented toward the radiation source. The installation of a collimator on such a guide with spherical surface has been published in DE 101 57 523 C1, which is hereby incorporated by reference. Certainly, this structure can be combined with a gantry or robot arm, so that control movements within a smaller range can be performed with this guide system and in a larger range with the gantry or the robot arm.

The design of the irradiation device may include that each iris diaphragm is equipped with a drive mechanism. Then, the design of the control unit may provide for adjusting the relevant aperture according to the divergence of rays. This may be useful, if the collimator with the iris diaphragms shall be supplied for installation in different types of irradiation devices so as to meet different distances to the radiation source. The control unit can be used to define how the apertures shall interact. In this way, the relevant differences in the divergence of rays can be considered by the program configuration. As an alternative, the iris diaphragms may be operated by means of one single drive mechanism. In this case, the control mechanism can adjust the relevant aperture according to the divergence of the rays. This requires less effort and possible programming errors can be excluded. This alternative is particularly useful, if the collimator with its iris diaphragms is permanently assigned to the same radiation source in an irradiation device.

One design variant specifies that the leaves of each iris diaphragm are controlled with at least one guide plate that includes one guide element of the linear guiding mechanism. The other guide element of the linear guiding mechanism is then located on the diaphragm leaves, e.g. on the above-stated bearing elements. The diaphragm leaves can be actuated by a cam disk that interacts with the diaphragm leaves and by a drive mechanism that initiates the adjustment movements of the diaphragm leaves by a relative rotational motion between guide plate and cam disk. In this manner, an adjustment movement of the cam disk will initiate simultaneous movement of all diaphragm leaves. Usually, the guide plate will be mounted stationary and the drive will be assigned to the cam disk for rotation.

In order to exclude any possible tilting of the diaphragm leaves it is useful to also move the leaves of each iris diaphragm with the help of a further guide plate on the opposite side.

If two iris diaphragms are to be used, the drive can engage between the two iris diaphragms and actuate both iris diaphragms from this position. This means, of course, that transmission of the adjustment movement to the diaphragm leaves may cause that the apertures are always different in size according to the divergence of rays. This may, for example, be realized by different designs of the force transmitting elements with different leverage of force transmission resulting in different adjusting distances for the setting of the iris diaphragms. One further possibility is to assign the drive to one iris diaphragm and to actuate the other iris diaphragm with the help of pins, whereby the force transmission elements, e.g. the cam disk, provide for suitable apertures so as to meet the divergence of the rays.

Of course, the design of the adjusting elements may also allow for several force transmissions by the drive. In this case, a gear unit can be assigned to at least one force transmission component that effects an opening of the aperture in relation to the divergence of rays. This offers the possibility of adjusting the collimator to different degrees of ray divergence by the exchange or modification of one transmission component of the gear. This is a special advantage, if an irradiation device shall be equipped with a collimator according to this invention at a later point in time. The setting can then be realized, for example, by the exchange of a gear wheel or a gear pair.

The cam disks may be provided with cam curves in a star-type arrangement that operate the bolt-type pins of the diaphragm leaves. The latter are usefully designed in the form of rollers, so as to ensure smooth operation.

One design variant of the irradiation device uses two six-leaf iris diaphragms displaced by 30° in the sense of rotation. This provides a regular dodecagon that comes close enough to the shape of a circle, so that calculation of the numerous single applications can be based on a circular cross-section of the relevant irradiation space.

These are only some preferred design variants, of course a regular dodecagon could also be achieved by arranging three four-leaf iris diaphragms on top of each other, or another number of diaphragm leaves and iris diaphragms could be selected.

BRIEF DESCRIPTION OF THE DRAWING

In the following, the invention is explained with the help of illustrations that show the principle layout and examples of design variants.

DESCRIPTION OF THE PREFERRED EMBODIMENT

Figure 1:
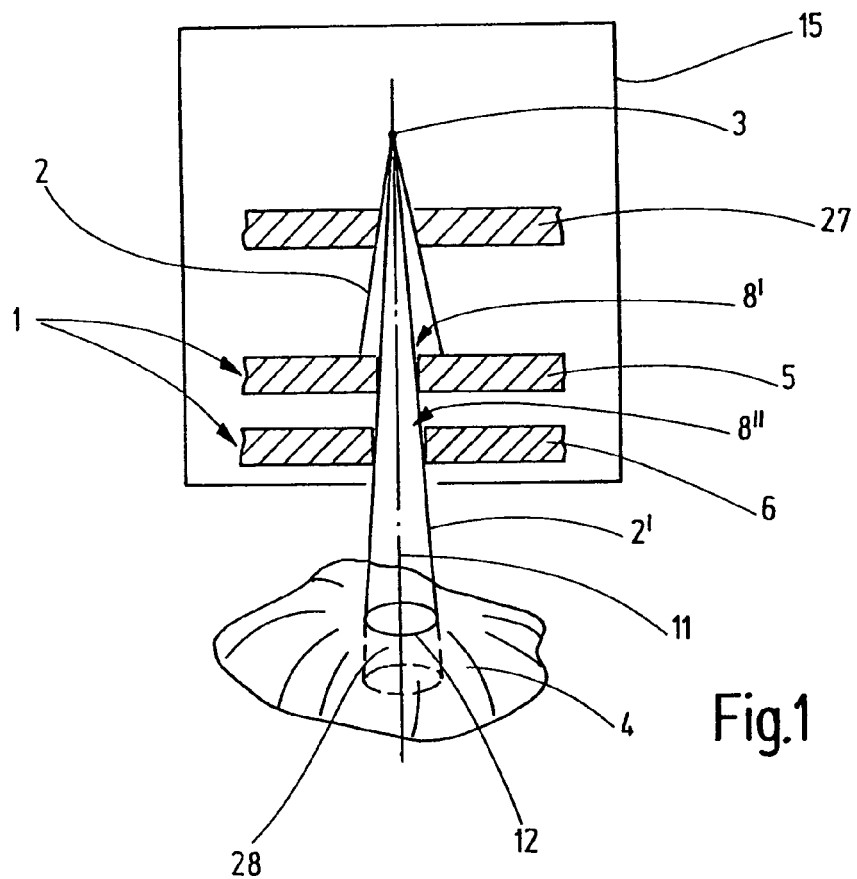
FIG. 1 is a schematic illustration of the cross section of an irradiation device as defined by the invention.

FIG. 1 shows a schematic illustration of the irradiation device, as defined by the invention, in a cross-sectional view. It shows the irradiation head 15 which includes a radiation source 3 and collimator 1 as defined by the invention. The drawing does not show the structure used to move the irradiation head 15 to different spatial positions. This structure may be a gantry, commonly-known in this field, which orientates the irradiation head 15 to an iso-center, so as to enable irradiation of an object to be treated 4, mostly a tumor, from all sides. When such a gantry is used, the focusing to the iso-center depends on its mechanical structure and variations are only possible by moving the patient, and thus the object to be treated 4. Instead of an orientation to one iso-center, the invention recommends a design variant with the irradiation head 15 being mounted on a robot arm that enables operation to all spatial coordinates and in any spatial angle alignment as far as is allowed by the mechanical construction of the robot arm. This allows a far greater degree of freedom and the different treatment positions can be reached much faster.

The radiation source 3 is, as usual, followed by a precollimator 27 which bundles the rays 2 in such a way that they cannot pass by the shielding area of the collimator 1. The central aspect of the invention is actually the collimator 1 that consists of at least two iris diaphragms 5 and 6 which are positioned in coaxial alignment relative to the radiation source 3. The axis 11 is marked by a dash-dotted line in the illustration and one can see how the rays 2 are restricted by the collimator 1, so that the collimated beam 2' forms a predefined irradiation space 28 within the area of the object to be treated 4. This is preferably effected by different opening sizes of the apertures 8', 8" of the iris diaphragms 5 and 6 according to the divergence of rays (indicated very exaggerated in the drawing) in order to collimate the beam 2' so that the cross-section of the beam 2' forms a polygon 12 the number of corners of which corresponds to the number of diaphragm leaves of all collimators 5 and 6. The latter is explained in more detail in the description of FIG. 2.

Figure 2:
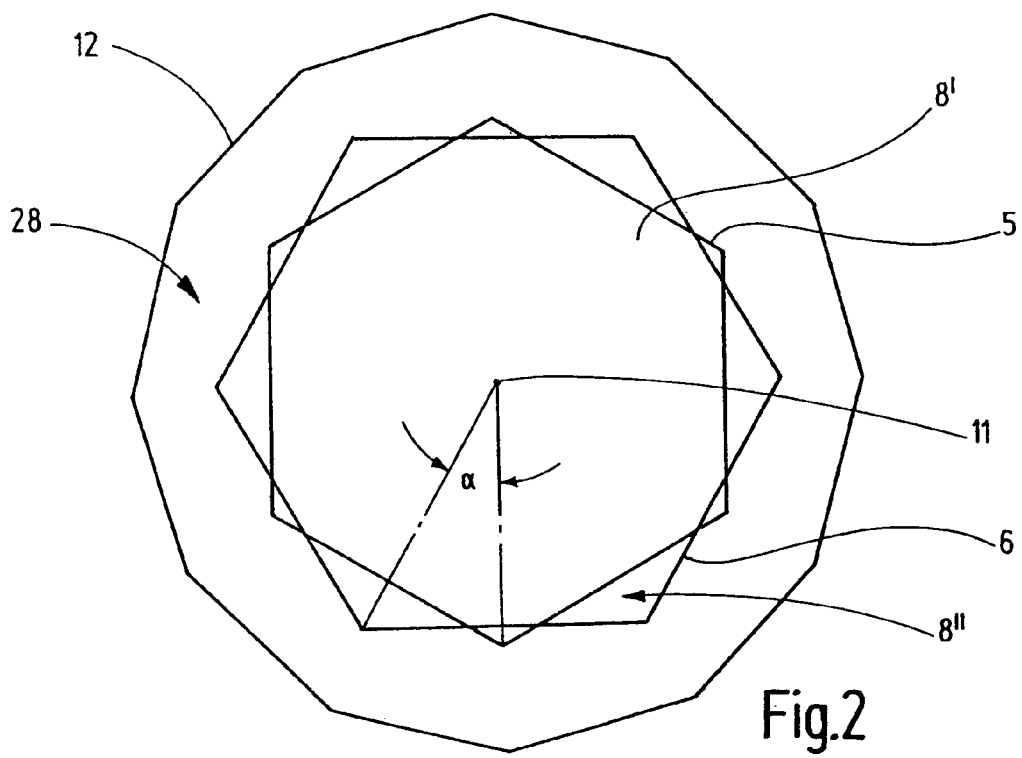
FIG. 2 is a schematic illustration that explains the functional principle of the collimator as defined by the invention.

FIG. 2 is a schematic illustration that explains the functional principle of the collimator 1, as defined by the invention. The iris diaphragms 5 and 6 shown in this illustration are six-leaf iris diaphragms 5, 6 so that hexagonal apertures 8' and 8" will be achieved. Through the displaced arrangement of the iris diaphragms 5, 6 by an angle α of 30° in rotational sense around the axis 11, the corners of one hexagon are centered exactly in the middle of the straight lines of the other hexagon. In this manner a polygon 12 is created, the number of corners of which corresponds to the number of leaves of all iris diaphragms. Because of the divergence of rays 2, the aperture 8' of the first iris diaphragm 5 is much smaller than the aperture 8" of the second iris diaphragm 6, so that the cross section of the beam 2' will have the shape of a regular dodecagon 12. Consequently, the irradiated space 28 will also have a dodecagonal shape, so that its cross section comes close to the shape of a circle or, respectively to the three-dimensional shape of a cylinder, so that the latter can be used for application calculation. Owing to the divergence of rays, the cross section of the irradiated space 28 will certainly be larger than the opening size of apertures 8' and 8". Compared to the beams 2' normally used, the apertures 8' and 8", as well as the polygon 12 are presented enlarged on the drawing.

According to the invention it is certainly possible to use further iris diaphragms instead of only the two iris diaphragms 5 and 6, and the use of iris diaphragms with a different number of leaves is also conceivable. In this case, however, a different angle displacement α must be selected so as to again achieve an equilateral polygon 12. Of course, all iris diaphragms must have the same number of leaves, as otherwise an equilateral polygon 12 could not be achieved.

Figure 3A:
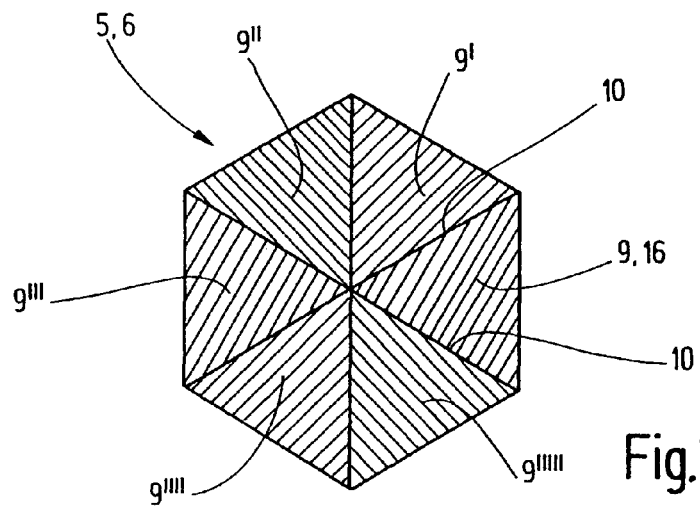
FIGS. 3a, 3b and 3c illustrate the layout principle to explain the function of an iris diaphragm as defined by the invention.
Figure 3B:
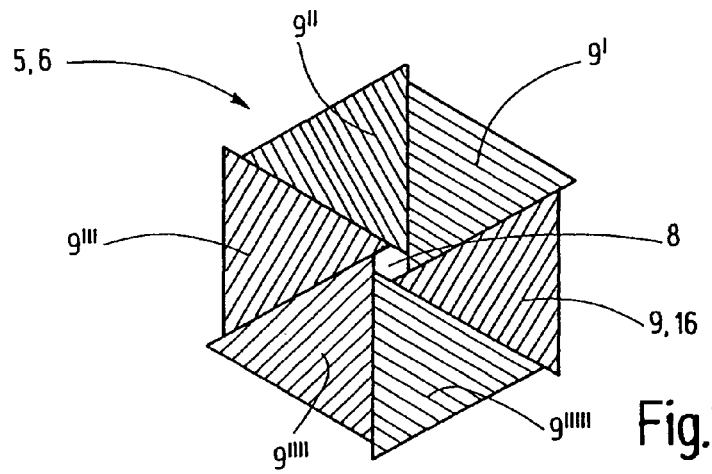
Figure 3C:
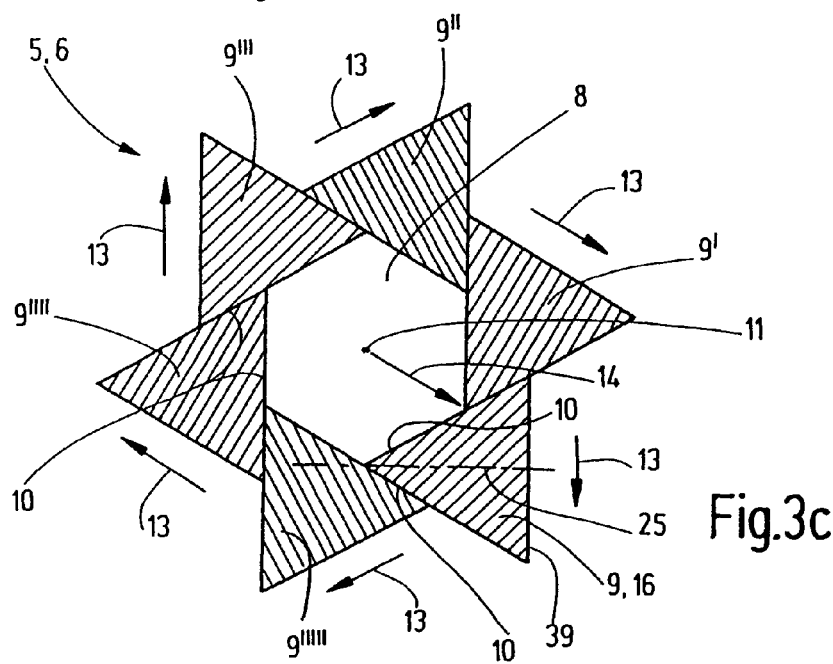

FIGS. 3a, 3b and 3c illustrate the functional principle of an iris diaphragm 5 or 6 as intended by the invention. FIG. 3a shows the iris diaphragm 5 or 6 in closed condition, in FIG. 3b it is shown with a small aperture 8 and in FIG. 3c the aperture 8 is opened to the maximum.

The illustrated iris diaphragm 5 or 6 is provided with six diaphragm leaves 9, 9', 9", 9''', 9'''' and 9''''', whereby the illustration only shows the shielding elements 16. In closed condition the side faces 10 of these diaphragm leaves 9, 9', 9", 9''', 9'''', 9''''' are positioned in such a way that they form the diagonals of a hexagon as shown in FIG. 3a. When an iris diaphragm 5, 6 is to be opened, the inner points of the diaphragm leaves 9, 9', 9", 9''', 9'''' and 9''''' that meet in FIG. 3a must be moved along the adjustment distance 14 which starts from the axis 11 and extends in outward direction as shown in FIG. 3c for the diaphragm leaf 9'. An adjustment distance 14 like this can be achieved when the diaphragm leaves 9, 9', 9", 9''', 9'''', 9''''' perform a straight movement in the direction of the arrows 13, i.e. in a direction perpendicular to the angle bisector 25 (relative to the side faces 10) as marked by the dot-dashed line in FIG. 3c. Certainly, all diaphragm leaves 9, 9', 9", 9''', 9'''', 9''''' must simultaneously perform exactly the same straight adjustment control movement 13. A possible example for the practical realization of such simultaneous adjustment movements 13 is described in the examples of design variants.

One major feature of the invention is the simple and straight control movement 13 which can be effected very easily by the setting of the aperture. An iris diaphragm 5, 6, for example, can be actuated with the help of a drive mechanism 19, or it is even possible to bring all iris diaphragms 5, 6 into the correct aperture position by means of only one drive mechanism 19. This relatively simple design of the adjusting element 7 offers the use of an irradiation head 15 of little volume and weight which is well suited to be handled by a robot arm of an adequately small construction size. This is of particular importance, since this allows use of robot arms already applied in other fields of engineering. This helps to avoid expensive special constructions and the irradiation device can be realized at relatively low costs.

Figure 4:
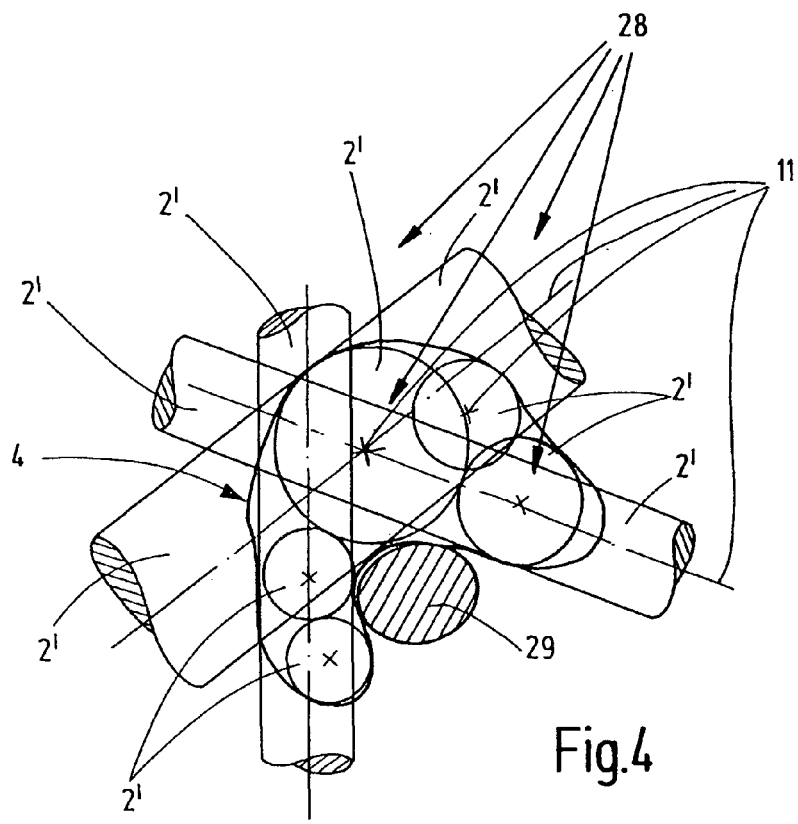
FIG. 4 illustrates the principle of radiation application with an irradiation device as defined by the invention.

FIG. 4 illustrates the principle of a radiation application by an irradiation device as defined by the invention. One decisive aspect of the working principle of the irradiation device is that the collimator 1 does not restrict the beam 2' in such a way that the outline of the irradiated space 28 corresponds to the outline of the object to be treated 4, e.g. the tumor, but that the outline of the object to be treated 4 is traced by a combination of irradiated spaces 28 of many single applications, whereby each application includes a beam 2' restricted by the collimator 1 with a cross-section in the form of a polygon 12 that comes close to a circle. FIG. 4 is a simplified illustration of how such single applications can be combined. It shows the object to be treated 4, e.g. a tumor, that is located in the direct vicinity of critical tissue, for example a nerve 29. In this case the beams 2' must be applied in such a way that the object to be treated 4 is exposed to a maximum radiation dose while the radiation dose applied to the surrounding tissue shall be as low as possible, so that the critical tissue 29 will be protected against direct irradiation. For this purpose, different apertures are used to irradiate partial spaces 28 of an approximately cylindrical shape that pass through the body in different single applications. At first, none of these partial spaces 28 must be focused directly to the critical tissue 29. With regard to the surrounding tissue, these single applications coming from many directions should not intersect, so that the surrounding tissue is exposed to a considerably lower amount of radiation than the object to be treated 4.

FIG. 4 shows a very simplified illustration of how the applications running parallel to the drawing plane—the axes 11 of the irradiated spaces 28 are marked by dot-dashed lines—and those running perpendicular to the drawing plane—the axes 11 of the irradiated spaces 28 are marked by crosses—can be used to obtain a multiple of the irradiation dose in the object to be treated 4. According to this simplified illustration, the intensity of radiation in the object to be treated 4 would, of course, be too low; consequently, this application must be performed in such a way that the irradiation intensity in the object to be treated 4 will be considerably higher. This is achieved by not only using radiation applications positioned in parallel and perpendicular to the drawing plane, but by radiation applications from all possible spatial angles. The term 'possible' in this context does not mean a geometrical restriction, but a limitation insofar that critical tissue 29, as in the illustrated example, shall be spared as far as possible. Under these conditions it is possible to expose the object to be treated 4 to a radiation dose suitable to destruct, for example, the tumor tissue while the surrounding tissue is exposed to a radiation dose so small that the tissue will be able to regenerate, or, apart from a few inevitable scattered rays, the critical tissue will be exposed only to very little or no radiation at all.

In view of the required multitude of overlaying partial spaces 28 to be irradiated from all sides by a great number of single applications one can imagine the enormous complexity of the required computation operations. If computation could not be based on polygons 12 that represent the cross-sections of the irradiated spaces 28 and which come so close to a circular shape that they can be calculated as a circle or respectively as cylinders in a three-dimensional area, the complexity of the procedure would soon exceed economic feasibility. This complexity results from the polygons to be considered, if the cross-section of the beams 2' would, for example, refer to squares or hexagons, and more so, if these polygons were in a different position for each application, so that computation would have to consider both the polygons, as well as their specific orientation. In view of the multitude of beam directions, the required computer capacity and computation time could not be managed with economically reasonable efforts. For this reason, the invention is based on the arrangement of at least two coaxial iris diaphragms which provides the precondition that the cross-sections of the beams 2' of the relevant polygons 12 allows to handle the irradiated spaces 28 of the single applications as cylinders without causing an inaccuracy that would be intolerable for the formation of an exact beam profile. On the other hand, the invention allows the use of iris diaphragms 5, 6 with a mechanical structure that is considerably simpler in design and easier to control than could be realized with an iris diaphragm provided with so many diaphragm leaves that a polygon 12 of the desired shape could be formed immediately.

The arrangement of iris diaphragms, as defined by the invention, offers a further advantage by the angle displacement which avoids that radiation leaking through the adjacent diaphragm leaves 9, 9', 9'', 9''', 9'''', 9''''' of the first iris diaphragm 5 will be fully shielded by the further iris diaphragm 6. Furthermore, the use of two iris diaphragms 5, 6 of this type offers a simple technique to set the apertures 8' and 8'' in such a way that the divergence of the beams 2' will be considered over the whole control range. This is of particular importance if the apertures 8, 8'' of the iris diaphragms shall be wide open—as shown in FIG. 4—in order to capture large areas of the object to be treated 4 with beams 2' of large diameters in the course of an application so that the overall treatment time will be considerably shortened.

Especially when applying beams 2' of large diameters, the use of identical apertures 8', 8'' would cause the occurrence of larger penumbrae which can be reduced by setting different apertures 8', 8'' adapted to the divergence of the beams 2' as can be seen in FIG. 1. This effect can be further intensified by bringing more than two iris diaphragms 5, 6 into the optical path, since the formation of penumbrae decreases with the number of iris diaphragms 5, 6 used to ½, ⅓ or ¼.

The very simplified illustration in FIG. 4 only explains the principle of how various beams 2' of different sizes can be used to increase the radiation dose within the completely irregular space of an object to be treated 4. Through the suitable overlaying of beams coming from all sides, the object to be treated 4 can be exposed to a multiple of the radiation dose than that illustrated in this drawing.

Figure 5:
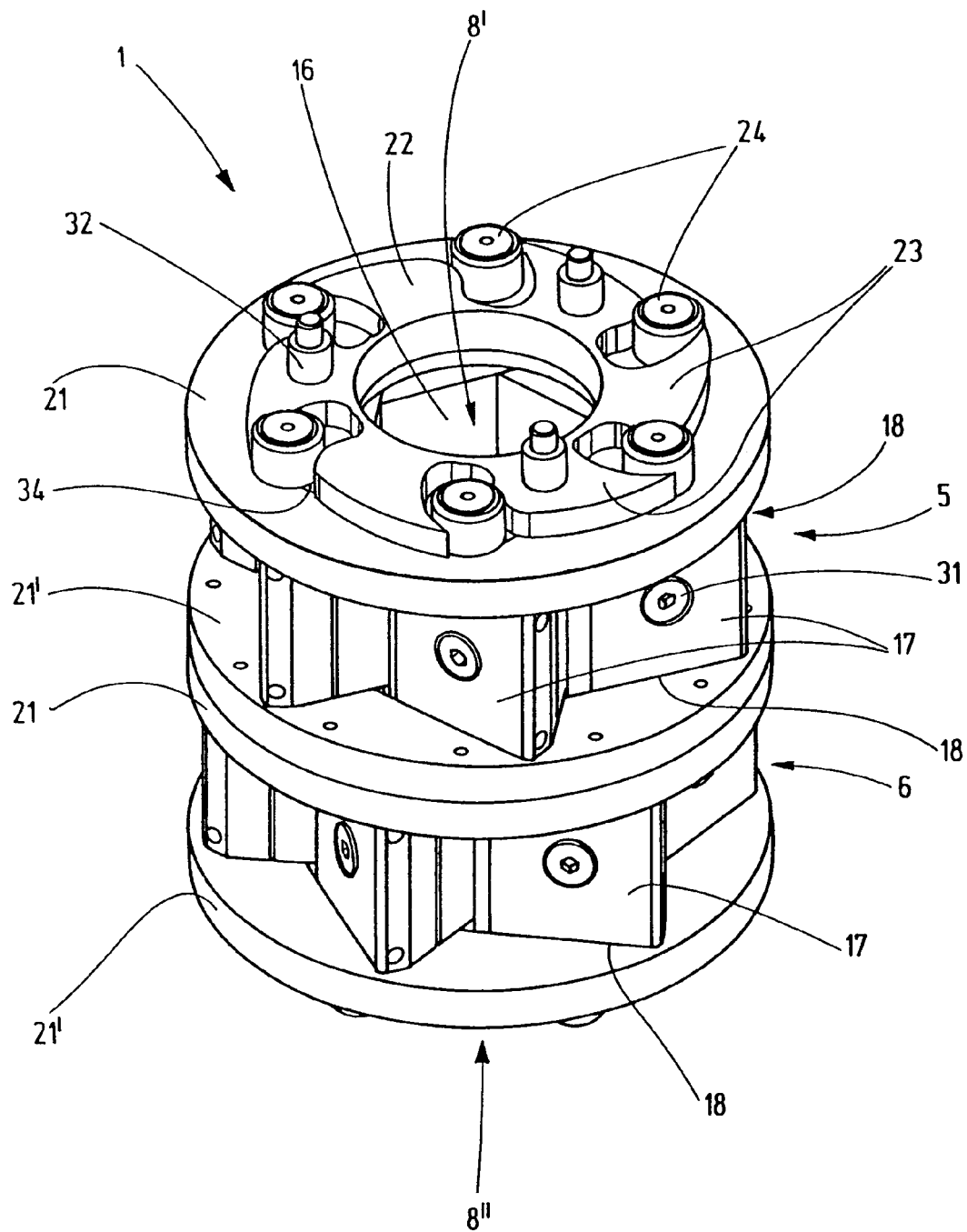
FIG. 5 shows a design example of a collimator as defined by the invention in a perspective view.

FIG. 5 shows, in a perspective view, an example of a design variant for the irradiation device as defined by the invention. The two iris diaphragms 5 and 6 are positioned in a coaxial arrangement on top of each other, so as to provide apertures 8' and 8'' of the type specified above. The structure of the diaphragm leaves 9, 9', 9'', 9''', 9'''', and 9''''' of the relevant iris diaphragms 5 and 6 complies with the arrangement described for FIG. 9. It consists of inside shielding elements 16 which can be seen through the opening on top, and of the outer bearing elements 17 which can be seen at the outline. The leaves 9, 9', 9'', 9''', 9'''', 9''''' of the iris diaphragms 5 and 6 are actuated via bolt-type drive pins 24 preferably of a roller-type form, which are operated by the cam curves 23 of a cam disk 22. The cam curves 23 are positioned in a star-type arrangement, so that each bolt-type drive pin 24 of each diaphragm leaf 9, 9', 9'', 9''', 9'''', 9''''' is assigned to such a cam curve 23.

The bolt-type pins 24 reach through the passing slots 34 of a guide plate 21 so as to transmit the adjustment movement to the diaphragm leaves 9, 9', 9'', 9''', 9'''', 9'''''. The bottom side of each iris diaphragm 5 and 6 is provided with a further guide plate 21' where the diaphragm leaves 9, 9', 9'', 9''', 9'''', 9''''' are also aligned with linear guides 18 so as to achieve a robust guide structure and, in particular, to avoid tilting of the leaves. The linear guides 18 consist of a guide element 18' on the diaphragm leaves 9, 9', 9'', 9''', 9'''', 9''''' and of a guide element 18'' positioned on a guide plate 21 that interacts with this guide element 18' and correspondingly on a further guide plate 21' (see FIGS. 7 and 9).

Figure 7:
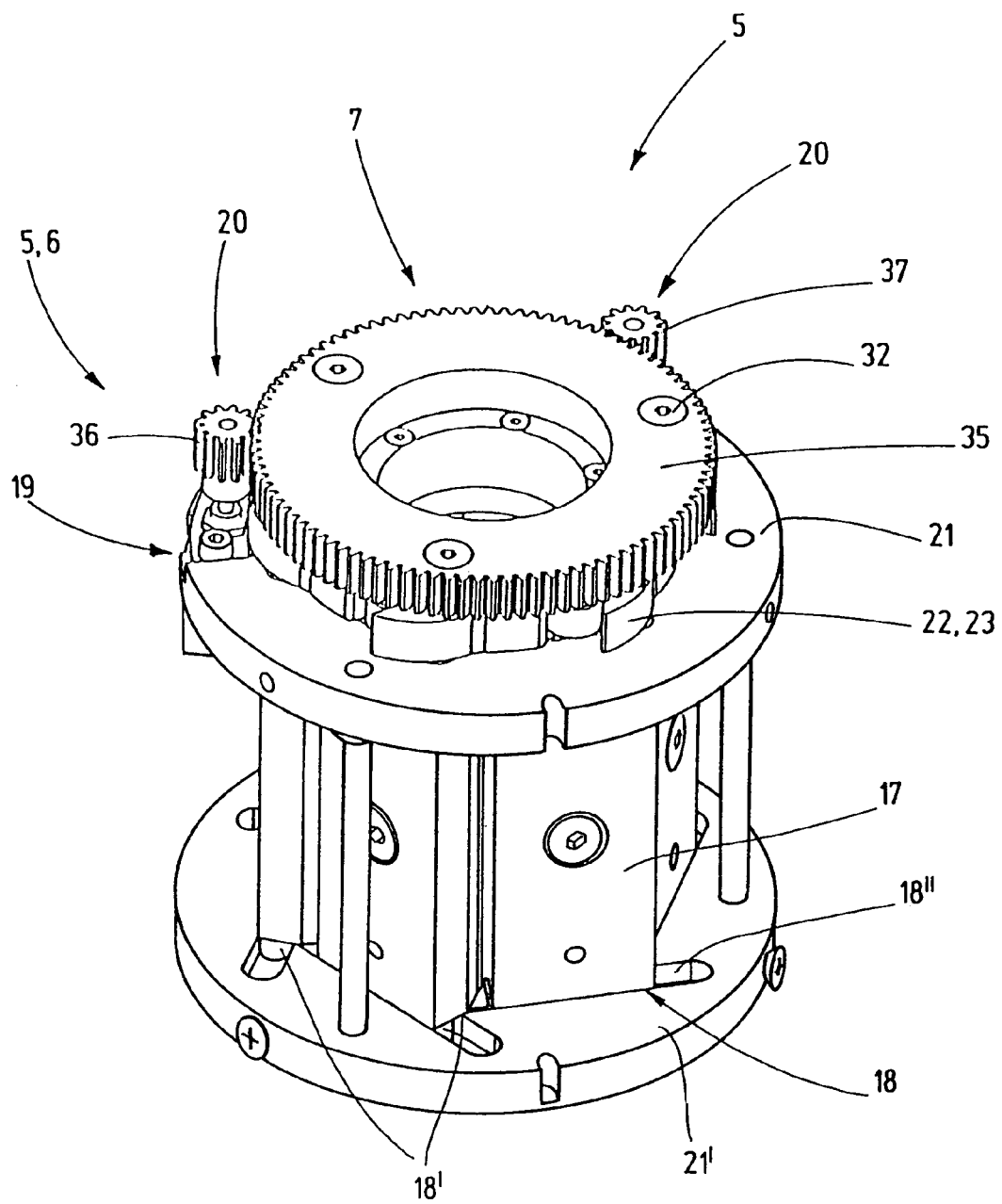
FIG. 7 shows an iris diaphragm with drive and gear mechanism.

The top side of cam disk 22 is provided with fixtures 32 for a drive mechanism, for example a pinion gear wheel 35 (see FIG. 7). The bottom side of the second iris diaphragm can also be allocated to a pinion gear wheel 35, or a control mechanism can be located between the two iris diaphragms 5, 6 that ensures that the control movement of one iris diaphragm 5 will be transmitted to the other iris diaphragm 6. The adjustment movements can be effected with the help of force transmission elements on the bottom side of the leaves 9, 9', 9'', 9''', 9'''', 9''''' of iris diaphragm 5. It is useful to define a ratio for transmission so that apertures 8' and 8'' of the iris diaphragms 5 and 6 will be adjusted to a size that meets the divergence of the rays 2. This can be effected, for example, with pins located on the leaves 9, 9', 9'', 9''', 9'''', 9''''' of one iris diaphragm 5 that reach into a cam disk 22 for the second iris diaphragm 6, whereby the pins engage in grooves positioned diagonal to the movement direction of the pins and that the required transmission ratio is effected by their inclination as required.

Figure 6:
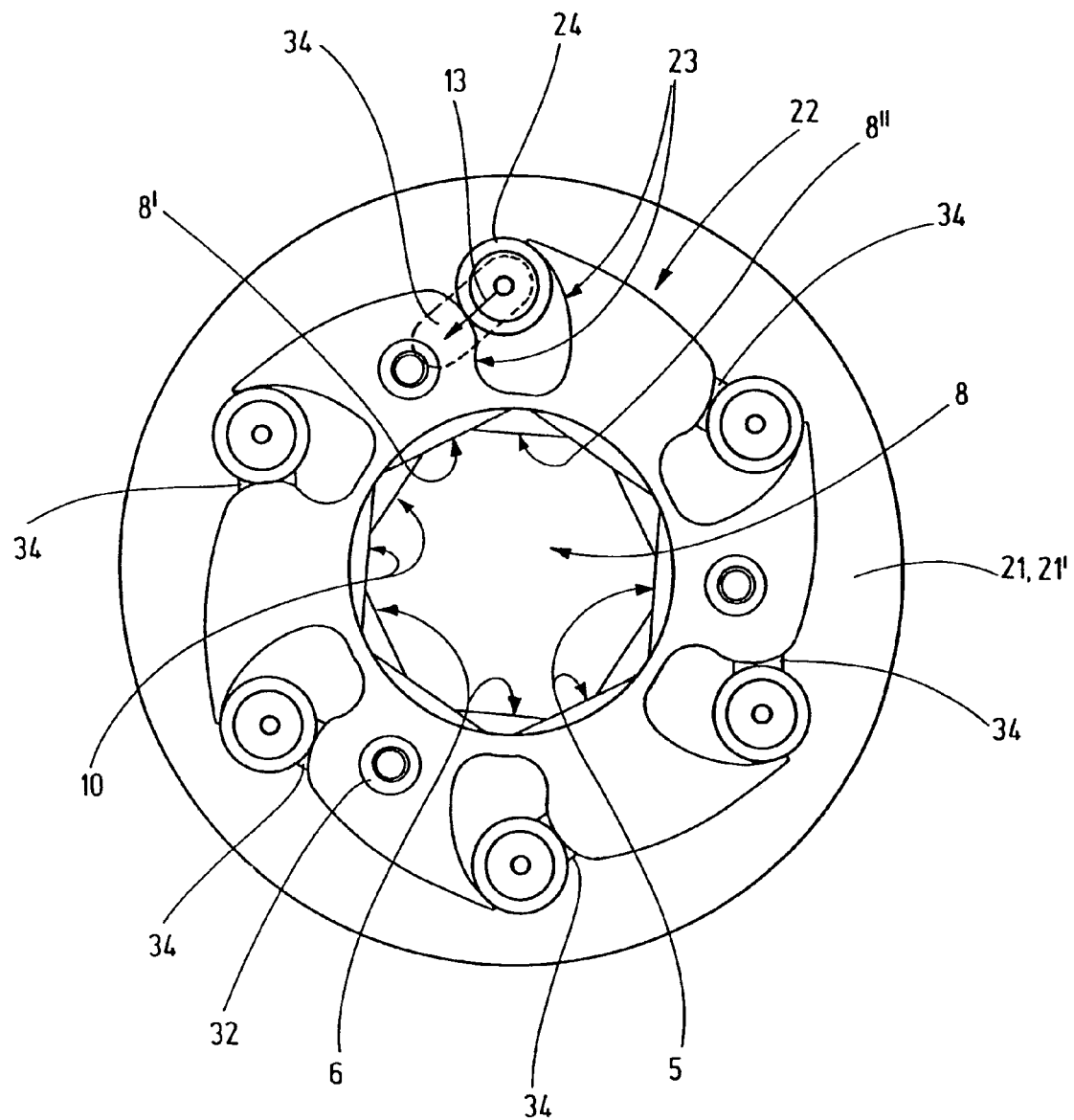
FIG. 6 shows a view of the collimator from top, as referred to in FIG. 5.

FIG. 6 shows the collimator 1 according to FIG. 5 in a view from the top. This illustration shows how the cam curves 23 of the cam disk 22 are operated, so that the bolt-type pins 24, including the diaphragm leaves 9, 9', 9'', 9''', 9'''', 9''''' connected to them, can be moved in the adjustment direction intended for one diaphragm leaf as indicated by the arrow 13. The adjustment movements 13 of all diaphragm leaves 9, 9', 9'', 9''', 9'''', 9''''' are performed as shown in FIG. 3c. These adjustment movements 13 are transmitted to the diaphragm leaves 9, 9', 9'', 9''', 9'''', 9''''' by means of bolt-type pins 24 which reach through the passing slots 34 of the guide plate 21 or a further guide plate 21'. In order to illustrate the shape of the passing slots 34, the top passing slot 34 is indicated by a dashed line in the drawing. Suitably matched to the relevant cam curves 23, all six passing slots 34 are operated accordingly.

In the area of aperture 8, both the aperture 8' of the first iris diaphragm 5 and the aperture 8'' of iris diaphragm 6 can be seen, as well as those parts of the side faces 10 of the diaphragm leaves 9, 9', 9'', 9''', 9'''', 9''''' which form the limits of the apertures 8' and 8''. On the upper side, the fixations 32 for a pinion gear wheel 35 can be seen.

FIG. 7 shows an iris diaphragm 5 with drive mechanism 19 and gear mechanism 20. The illustration corresponds basically to that of FIG. 5, except that it shows only one of the two iris diaphragms 5, 6. In this illustration, the pinion gear wheel 35 is attached to the cam disk 22 with fixtures 32 so as to actuate the adjustment movement. Starting from the drive mechanism 19, a first pinion 36 of the gear mechanism 20 reaches into the pinion gear wheel 35 and, with the help of a shaft, a second pinion 37 is positioned which transmits the drive force to a further pinion gear wheel 35 allocated to the second iris diaphragm 6 (which is not shown in this illustration). With a gear mechanism 20 of this type, the transmission for each iris diaphragm 5 or 6 can be simply varied by replacing the pinions 36 or 37 and the pinion gear wheel 35 by other ones with a different number of teeth. In this way, a collimator 1 can be easily adapted to another irradiation device with a different divergence of rays.

FIG. 7 also provides a better view of the linear guides 18 for the bearing elements 17 of the diaphragm leaves 9, 9', 9'', 9''', 9'''', 9''''', since the aperture of iris diaphragm 5 is not opened to maximum size as in FIG. 5. Here one can see how the guide elements 18' of the diaphragm leaves 9, 9', 9'', 9''', 9'''', 9''''' move along the guide element 18'' of the guide plate 21'. This can, however, be seen only on the further guide plate 21', although the same principle applies to the upper guide plate 21.

Figure 8:
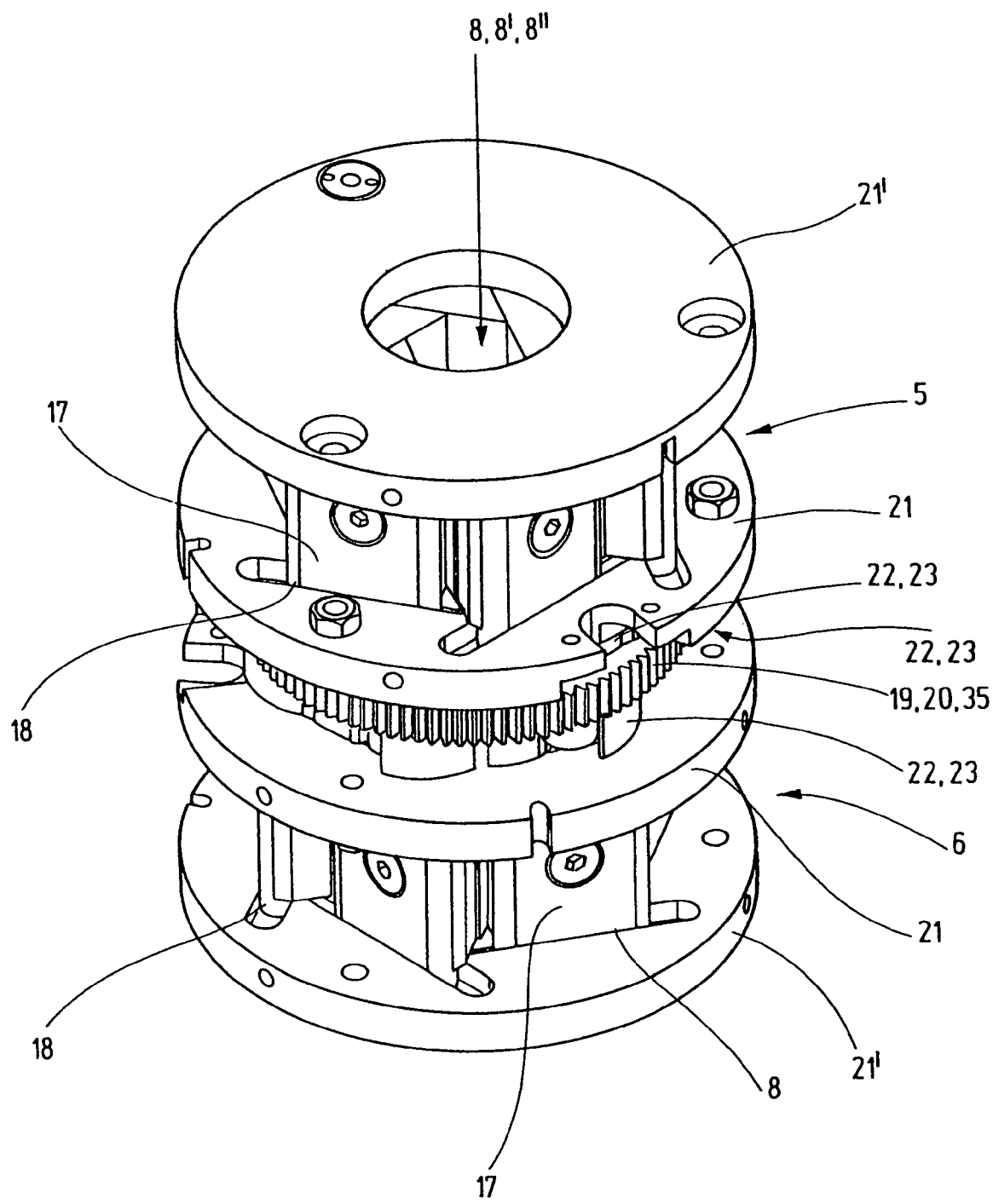
FIG. 8 shows a further design example of a collimator, as defined by the invention, with a drive mechanism arranged between two iris diaphragms

FIG. 8 shows a further example of a design variant for the collimator 1, as defined by the invention with a drive mechanism 19 positioned between the two iris diaphragms 5, 6.

With this variant, one single pinion gear wheel 35 is positioned between two cam disks 22 each of which is assigned to one of the iris diaphragms 5 and 6. Again, a pinion (not shown in this illustration) uses the drive mechanism 19 to engage in the pinion gear wheel 35, so as to achieve a gear mechanism 20 for the adjustment movement. In this case the pinion gear wheel 35 performs the same adjustment movements for the two iris diaphragms 5 and 6, the adjustment distances 14, which should be different for the two iris diaphragms 5 and 6 according to the divergence of rays 2, must be realized with the help of cam curves 23 of the cam disks 22, which are formed differently for each of the iris diaphragms 5 and 6 and/or the inclination of the through-passing slots 34 must be shaped differently. Differently, in this context, means that different adjusting distances are transmitted to the bolt-type pins 24, even when the adjustment angles of the iris diaphragms 5 or 6 are identical. This can be effected, for example, by the use of cam disks 22 of different size to move the pins 24 of the iris diaphragms 5, 6 over different distances by actuating different leverages so as to enable a transmission ratio for the apertures 8, 8' of the iris diaphragms 5, 6 that complies with the divergence of rays. All other reference signs refer to the same parts as described above.

Figure 9:
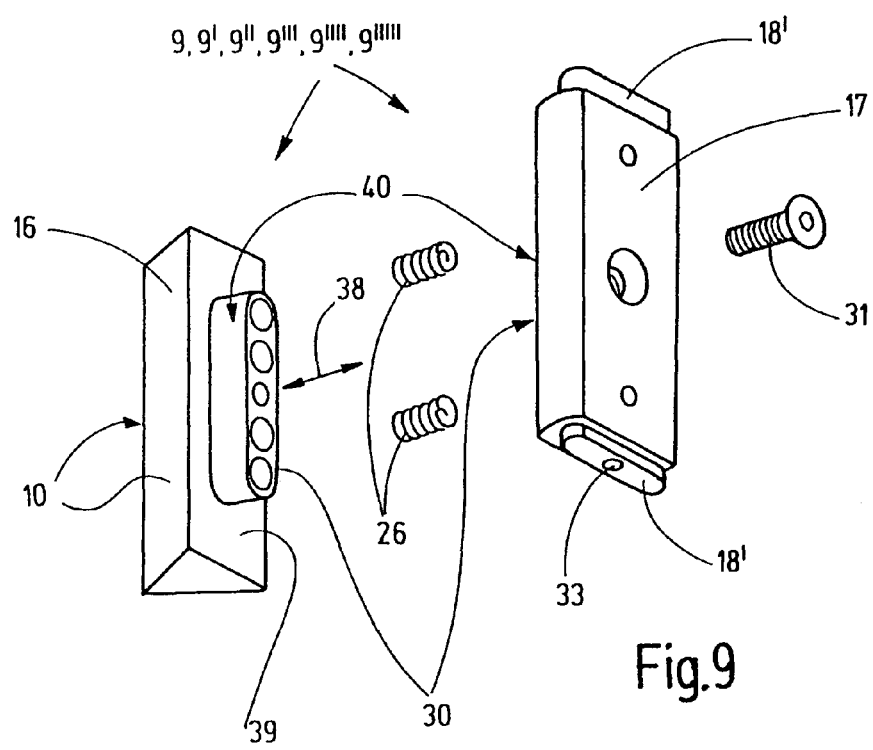
FIG. 9 shows a very favorable design of the leaf of an iris diaphragm for a collimator as defined by the invention.

FIG. 9 shows the structure of a diaphragm leave 9, 9', 9'', 9''', 9'''' or 9''''' that is particularly favorable for a collimator 5 or 6 as defined by the invention. The diaphragm leaf 9, 9', 9'', 9''', 9'''' or 9''''' is provided with a shielding element 16 that is mounted to a bearing element 17 with the help of a support element 30. This support element 30 is equipped with a guide 40 (only visible on the shielding element 16, a groove complementary to the visible support element 30 is located at the bearing element 17) and it is provided with springs 26 and a screw 31, that enables a spring motion in the direction of the double arrow 38 so that the shielding element 16 rests on the bearing element 17 with a spring-type support. This construction makes sure that the side faces of the shielding elements 16 of all diaphragm leaves 9, 9', 9'', 9''', 9'''', 9''''' will always lay evenly in relation to each other. The support 30 is located on the rear surface 39 of the shielding element 16. (To illustrate its location, this rear surface 39 is shown in FIG. 3c for the diaphragm leaf 9.) Inspection of FIGS. 9 and 3c shows that the spring force applied to the diaphragm leave 9 in the direction of the angle bisector 25 is divided into two equal force components extending in the direction of the diaphragm leaves 9' and 9'''''. The same principle applies to each diaphragm leaf 9, 9', 9'', 9''', 9'''', 9'''''. The size of the shielding elements 16 is adjusted to the rays 2, so that the whole beam will be shielded even if the iris diaphragm 5 or 6 is closed (see FIG. 3a). The rays 2 will be restricted by the precollimator 27 (see FIG. 1).

The bearing element 17 of the diaphragm leaves 9, 9', 9'', 9''', 9'''', 9''''' is provided with two guide elements 18' which interact with the guide elements 18" of the guide plate 21 and the further guide plate 21'. At least one of these guide elements 18' is provided with a fixation thread 33 for a pin 24 that reaches through a passing slot 34 of a guide plate 21 or 21', using the cam disk 22 to produce a connection to the drive mechanism 19.

The special significance of the design of the diaphragm leaves 9, 9', 9'', 9''', 9'''', 9''''' including shielding element 16 and bearing element 17 has been explained above, i.e. an even positioning of all side faces 10 can be achieved even in the case of deviations in tolerance. This is, of course, only one possible construction model. Other design variants are also conceivable, such as arrangement of an elastic material between the shielding element 16 and the bearing element 17.

The illustrations only depict one of many possible design variants of the invention: certainly the drive mechanisms and the diaphragm leaves 9, 9', 9'', 9''', 9'''', 9''''' could also be designed in a different manner. A different type of linear guiding would also be conceivable as, for example, the guiding of the bolt-type pins 24 in spiral-type curves. As already mentioned above, more than the two iris diaphragms 5, 6 could be used and it is also possible to use iris diaphragms with a different number of leaves. The ultimate essence of the invention is, that at least two iris diaphragms 5, 6 are arranged in such a way so that a polygon 12 can be achieved even with a limited number of diaphragm leaves 9, 9', 9'', 9''', 9'''', 9''''' that comes very close to the shape of a circle, so as to enable the above-described exact radiation application at a relatively short treatment period, while reducing leakage radiation emitting between the diaphragm leaves 9, 9', 9'', 9''', 9'''', 9''''' to a minimum.

LIST OF REFERENCE NUMBERS

1 Collimator
2 Rays
2' Beam restricted by the collimator (with an essentially circular beam cross-section)
3 Radiation source
4 Object to be treated
5 Iris diaphragm
6 Further iris diaphragm
7 Adjusting element
8, 8', 8" Aperture
8' of the first iris diaphragm 5
8" of the second iris diaphragm 6
9, 9', 9", 9'"
9"", 9""' Leaves of a six-leaf iris diaphragm
10 Side faces
11 Axis
12 Polygon (formed by the collimator)
13 Arrows: linear adjustment movement
14 Adjustment distances
15 Irradiation head
16 Shielding element of the diaphragm leaves
17 Bearing element of the diaphragm leaves
18 Linear guides
18' Guide element on the diaphragm leaves
18" Guide element on the guide plate
19 Drive mechanism
20 Gear mechanism
21 Guide plate
21' Further guide plate
22 Cam disk
23 Cam curves, in star-type arrangement
24 Bolt-type pin, preferably rollers
25 Angle bisector between the side faces 10
26 Springs between shielding element and bearing element
27 Precollimator
28 Irradiated space, partial space
29 Critical tissue (e.g. a nerve)
30 Support element
31 Screw
32 Fixture for pinion gear wheel
33 Fixation thread for pin 24
34 Passing slot for pin 24
35 Pinion gear wheel
36 First pinion
37 Second pinion
38 Double arrow: direction of spring motion
39 Rear surface of a shielding element
40 Guide
$\alpha$ Displacement of the iris diaphragm in rotational sense around the axis 11

I claim:

1. An irradiation device to define a beam of high-energy rays proceeding from an essentially punctiform radiation source and directed to an object to be radiation treated or to be treated by stereotactic conformation radiotherapy of tumors, the device comprising:
a first iris diaphragm collimator having adjusting elements to provide variable apertures for beam collimation;
at least one second iris diaphragm collimator disposed in coaxial alignment with an optical path, wherein leaves of said first and said second collimators iris diaphragms are arranged in a staggered manner and in a rotational sense around an axis, so that the beam limited by the collimators has a cross-section of a polygon, the number of corners of which equals a total number of the leaves of all iris diaphragm collimators, said leaves having adjacent side faces enclosing same angles, wherein adjustment movements of said diaphragm leaves are linearly perpendicular to an angle bisector of side faces engaged in adjacent diaphragm leaves; and
a control mechanism to direct, from all sides, the beams limited by said collimators towards the object to be treated, wherein parameters for direction, surface area, intensity and time of irradiation are controlled in such a manner that a three-dimensional dosing profile for radiation application is achieved, said control mechanism being suitable to irradiate an irregular space with many overlaying and adjoining irradiated spaces.

2. The irradiation device of claim 1, wherein adjusting elements of said iris diaphragms are designed such that beam collimation by respective apertures corresponds to a divergence of the beams within an overall adjusting range.

3. The irradiation device of claim 1, wherein an identical number of leaves of at least two iris diaphragms allows an angle displacement ($\alpha$) of said iris diaphragms in a same rotational sense around axes thereof, wherein a design of adjusting elements of said iris diaphragms with identical adjustment distances for said diaphragm leaves of a respective iris diaphragm is such that a cross-section of an equilateral polygon of the beam is formed throughout an entire setting range.

4. The irradiation device of claim 1, wherein said control mechanism generates different individual applications by use of different apertures and through positioning of the radiation source and said collimators in a three-dimensional area as well as through alignment thereof at specific spatial angles, wherein a combination of a multitude of said irradiation spaces of individual applications that capture only limited partial spaces of the object to be treated and which have a mainly circular beam cross-section are used to trace an irregular shape of the object to be treated, wherein multiple adjoining and overlaying irradiation spaces, including only partly adjoining and overlaying irradiation spaces, are irradiated within a area of the object to be treated by individual applications, so that the object to be treated can be irradiated within substantially exact borders and with a predefined intensity that is considerably higher than that applied to the surrounding tissue.

5. The irradiation device of claim 3, wherein said individual applications are performed with unchanged parameters within a certain period of time.

6. The irradiation device of claim 1, wherein application of force presses the side faces of said diaphragm leaves against each other.

7. The irradiation device of claim 6, wherein said diaphragm leaves consist essentially of a shielding element made of shielding material and a bearing element, said bearing element having a linear guiding mechanism with a guide element for adjustment movement, wherein said shielding element is supported with a spring on said bearing element to be pressed evenly towards a direction of adjacent diaphragm leaves.

8. The irradiation device of claim 1, further comprising an irradiation head which includes the radiation source and said collimator and which is positioned on a gantry.

9. The irradiation device of claim 1, further comprising an irradiation head having the radiation source and said collimator, said irradiation head being mounted to a robot arm to bring said irradiation head into any spatial position and angular alignment.

10. The irradiation device of claim 1, wherein said collimators are installed on a track with a spherical surface, so that they can be shifted in all directions for sluing motions within a limited spatial angle range, wherein an axis is always oriented toward the radiation source.

11. The irradiation device of claim 1, wherein each iris diaphragm is equipped with a drive mechanism.

12. The irradiation device of claim 11, wherein said control mechanism adjusts a respective said aperture according to a divergence of the beam.

13. The irradiation device of claim 1, wherein said iris diaphragms are actuated by one single drive mechanism.

14. The irradiation device of claim 13, wherein said control mechanism operates a respective aperture according to a divergence of the beam.

15. The irradiation device of claim 14, wherein said drive mechanism is allocated to said first iris diaphragm and said second iris diaphragm is actuated by means of pins, wherein force transmitting elements are suitable to actuate a respective said aperture so as to conform to a divergence of the beam.

16. The irradiation device of claim 13, wherein said drive mechanism engages between two said iris diaphragms to operate both said iris diaphragms from an engagement position.

17. The irradiation device of claim 13, wherein adjusting elements are suitable for several force applications to said drive mechanism.

18. The irradiation device of claim 17, wherein at least one force application is allocated to a gear mechanism, so that a relation between the apertures is achieved which conforms to a divergence of the beam.

19. The irradiation device of claim 18, wherein at least one gear mechanism is provided with at least one exchangeable or adjustable transmission element to enable setting of said collimators to different ray divergences.

20. The irradiation device of claim 1, wherein said leaves of each said iris diaphragm are controlled by at least one guide plate that includes one guide element of a linear guide mechanism.

21. The irradiation device of claim 20, wherein a cam disk interacts with said diaphragm leaves and a drive mechanism actuates adjustment movements of said diaphragm leaves by means of a relative rotational movement between said guide plate and a cam disk.

22. The irradiation device of claim 21, wherein said cam disks are provided with cam curves positioned in star-type arrangement which are suitable to actuate bolt-type pins of said diaphragm leaves.

23. The irradiation device of claim 22, wherein said bolt-type pins are formed as rollers.

24. The irradiation device of claim 20, wherein said diaphragm leaves of each iris diaphragm are also guided on an opposite side by means of a further guide plate.

25. The irradiation device of claim 1, wherein two six-leaf iris diaphragms are arranged at a displacement angle of 30° in a rotational sense thereof.

26. A collimation device to define a beam of high-energy rays proceeding from an essentially punctiform radiation source and directed to an object to be radiation treated or to be treated by stereotactic conformation radiotherapy of tumors, the device comprising:
 a first iris diaphragm collimator having adjusting elements to provide variable apertures for beam collimation; and
 at least one second iris diaphragm collimator disposed in coaxial alignment with an optical path, wherein leaves of said first and said second collimators iris diaphragms are arranged in a staggered manner and in a rotational sense around an axis, so that the beam limited by the collimators has a cross-section of a polygon, the number of corners of which equals a total number of the leaves of all iris diaphragm collimators, said leaves having adjacent side faces enclosing same angles, wherein adjustment movements of said diaphragm leaves are linearly perpendicular to an angle bisector of side faces engaged in adjacent diaphragm leaves.

27. The collimator of claim 26, wherein an identical number of leaves of at least two iris diaphragms allow an angle displacement ($\alpha$) of said iris diaphragms in a same rotational sense around an axis thereof, wherein design of iris diaphragm adjusting elements includes identical adjustment distances for said diaphragm leaves of a respective iris diaphragm, so that a beam cross-section of an equilateral polygon will be formed throughout a setting range.

28. The collimator of claim 26, wherein an application of force presses said diaphragm leaves against each other.

29. The collimator of claim 26, wherein said diaphragm leaves consist essentially of a shielding element made of shielding material and a bearing element, said bearing element having a linear guiding mechanism with a guide element for adjustment movement, said shielding element being supported on said bearing element with springs to be evenly pressed in a direction towards adjacent diaphragm leaves.

* * * * *